(12) United States Patent
Maule et al.

(10) Patent No.: US 9,888,167 B2
(45) Date of Patent: Feb. 6, 2018

(54) SELECTABLE ENHANCEMENT WINDOW FOR INCREMENTAL MEASUREMENT ADJUSTMENT

(71) Applicant: General Electric Company, Schenectady, NY (US)

(72) Inventors: Bryan David Maule, Camillus, NY (US); Daniel McClung, Syracuse, NY (US); Melissa Rose Stancato, Syracuse, NY (US); Thomas Charles Ward, Auburn, NY (US)

(73) Assignee: General Electric Company, Schenectady, NY (US)

( * ) Notice: Subject to any disclaimer, the term of this patent is extended or adjusted under 35 U.S.C. 154(b) by 697 days.

(21) Appl. No.: 14/292,680

(22) Filed: May 30, 2014

(65) Prior Publication Data
US 2015/0350534 A1 Dec. 3, 2015

(51) Int. Cl.
*G06F 3/0484* (2013.01)
*H04N 5/232* (2006.01)
*G01N 29/22* (2006.01)

(52) U.S. Cl.
CPC ....... *H04N 5/23216* (2013.01); *G01N 29/226* (2013.01); *G06F 3/04842* (2013.01); *G06F 3/04845* (2013.01); *G06F 3/04847* (2013.01)

(58) Field of Classification Search
CPC .................................................. G06F 3/04842
See application file for complete search history.

(56) References Cited

U.S. PATENT DOCUMENTS

| 5,073,819 | A  | * | 12/1991 | Gates | G01C 15/00 345/421 |
| 5,864,601 | A  |   | 1/1999  | Cattorini et al. | |
| 7,124,053 | B2 | * | 10/2006 | Tanaka | G06T 7/80 702/152 |
| 7,564,626 | B2 |   | 7/2009  | Bendall et al. | |
| 7,705,908 | B2 | * | 4/2010  | Fredlund | H04N 1/02409 348/222.1 |

(Continued)

OTHER PUBLICATIONS

PCT Search Report and Written Opinion issued in connection with corresponding PCT Application No. PCT/US2015/030090 dated Jul. 17, 2015.

(Continued)

*Primary Examiner* — William Bashore
*Assistant Examiner* — Nathan Shrewsbury
(74) *Attorney, Agent, or Firm* — Fletcher Yoder, P.C.

(57) ABSTRACT

A system includes an image capture device configured to capture an image of at least a portion of an industrial device or machinery. The system also includes a display configured to display the image. The system further includes a processor communicatively coupled to the image capture device and the display and configured to cause the display to display a graphical user interface (GUI) on the display, wherein the GUI comprises a first indicator located in user selectable first portion of the display and a window configured to display a portion of the image corresponding to a location of the first indicator, wherein the processor is configured to cause the first indicator to move to a second portion of the display in response to receiving an indication of a user interaction with the window.

20 Claims, 3 Drawing Sheets

(56) References Cited

U.S. PATENT DOCUMENTS

| | | | |
|---|---|---|---|
| 8,649,557 B2 * | 2/2014 | Hyung | G06T 7/277 382/103 |
| 8,873,837 B2 * | 10/2014 | Jahanshahi | G06K 9/00624 382/155 |
| 8,896,686 B2 * | 11/2014 | Chen | G01C 11/00 348/116 |
| 2009/0147023 A1 * | 6/2009 | Jetha | G06F 3/04845 345/620 |
| 2010/0189325 A1 * | 7/2010 | Garg | G06K 9/4604 382/131 |
| 2010/0231721 A1 * | 9/2010 | Meloche | G08G 5/065 348/159 |
| 2011/0001809 A1 * | 1/2011 | McManus | G01J 5/02 348/61 |
| 2011/0007873 A1 | 1/2011 | Rudin | |
| 2011/0141103 A1 | 6/2011 | Cohen et al. | |
| 2011/0320978 A1 | 12/2011 | Horodezky et al. | |
| 2012/0257068 A1 * | 10/2012 | Imai | H04N 5/23212 348/207.11 |
| 2012/0321128 A1 * | 12/2012 | Medioni | G06K 9/00771 382/103 |
| 2014/0028608 A1 | 1/2014 | Habermehl et al. | |
| 2014/0104100 A1 * | 4/2014 | Kubota | G01S 7/066 342/182 |
| 2014/0241573 A1 * | 8/2014 | Goel | G06K 9/6217 382/103 |
| 2014/0276055 A1 * | 9/2014 | Barthe | A61N 7/02 600/439 |
| 2014/0354466 A1 * | 12/2014 | Nomura | G01S 7/04 342/104 |
| 2015/0078122 A1 * | 3/2015 | Langford-Wood | G01S 7/56 367/7 |

OTHER PUBLICATIONS

U.S. Appl. No. 14/292,771, filed May 30, 2014, Chen Goldberger.

U.S. Appl. No. 14/292,648, filed May 30, 2014, Clark Alexander Bendall.

U.S. Appl. No. 14/292,840, filed May 31, 2014, Ritwick Jana.

U.S. Appl. No. 14/292,651, filed May 30, 2014, Bryan David Maule.

* cited by examiner

SELECTABLE ENHANCEMENT WINDOW FOR INCREMENTAL MEASUREMENT ADJUSTMENT

BACKGROUND

The subject matter disclosed herein relates to non-destructive testing devices, and more specifically, to providing selectable functionality of displayed images to facilitate the use of the non-destructive testing devices.

Certain devices may be used to inspect a variety of systems and facilities, such as power generation equipment and facilities, oil and gas equipment and facilities, aircraft equipment and facilities, manufacturing equipment and facilities, and the like. The inspection equipment may include various non-destructive inspection or non-destructive testing (NDT) devices. For example, video boroscopes (or endoscopes), portable eddy current inspection devices, portable X-ray inspection devices, and the like, may be used to observe or otherwise inspect the systems and facilities using non-destructive inspection techniques. These devices may display a video picture of an object situated within a remote cavity.

The image displayed by the NDT devices may be displayed on a video screen and may vary in magnification, apparent size, and detail, depending upon how close the end of the insertion tube carrying the lens system is from the object being viewed. Likewise, particular regions of the image may be presented as a magnified portion in the display. Additionally, the NDT devices may include user interfaces useful in allowing users to perform various monitoring functions. Unfortunately, such user interfaces may be complex, cumbersome, and time-consuming for users. Additionally, these user interfaces may not allow for ease of viewing of an enhanced portion of an image. Accordingly, it may be useful to provide NDT devices with improved user interfaces.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a portable non-destructive testing (NDT) device, includes a processor configured to receive imaging data captured via a sensor of the NDT device, cause a display of the NDT device to display an image to be analyzed based on the imaging data, cause the display to display a graphical user interface (GUI), wherein the GUI comprises a first indicator located in user selectable first portion of the display and a window configured to display a portion of the image corresponding to a location of the first indicator, and cause the first indicator to move to a second portion of the display in response to receiving an indication of a user interaction with the window.

In a second embodiment, a non-transitory computer-readable medium having computer executable code stored thereon, the code comprising instructions to receive captured imaging data, generate image data for display of an image on a display based on the captured imaging data, generate a graphical user interface (GUI) for display on the display in conjunction with the image data, wherein the GUI comprises a first indicator located in a user selectable first portion of the display and a window configured to display a portion of the image corresponding to the location of the first indicator, and modify the GUI to cause the first indicator to move to a second portion of the display in response to receiving an indication of a user interaction with the window.

In a third embodiment, a system includes a camera configured to capture an image of at least a portion of an industrial device or machinery, a display configured to display the image, and a processor communicatively coupled to the camera and the display and configured to cause the display to display a graphical user interface (GUI) on the display, wherein the GUI comprises a first indicator located in a user selectable first portion of the display and a window configured to display a portion of the image corresponding to a location of the first indicator, wherein the processor is configured to cause the first indicator to move to a second portion of the display in response to receiving an indication of a user interaction with the window.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Present embodiments relate to a non-destructive testing (NDT) device (e.g., video boroscope) useful in presenting enhanced (e.g., magnified) images in conjunction with a video image. The magnification images may be presented in a magnification window and may allow for user input to adjust icons on the image separate from the magnification image. In this manner, a graphical user interface may allow for precise movements of a cursor or other indicator in a portion of a primary image via inputs received in the magnification window (e.g. in a portion of the display separate from the image of the indicator on a primary image), whereby the magnification window includes a magnified portion of the primary image that corresponds to the location of the indicator. In some embodiments, this may allow for fine-tuning of the movements of the cursor or other indicator. In this way, the user (e.g., operator, technician, engineer, and so forth) may be able to view a primary image and modify a portion that is magnified without impacting the ability to view the primary image while altering the portion that is magnified. This may allow for greater ease of interaction with the NDT device's graphical user interface (GUI), thus facilitating and improving the use and user-friendliness of such devices in various testing and inspection applications.

Figure 1:
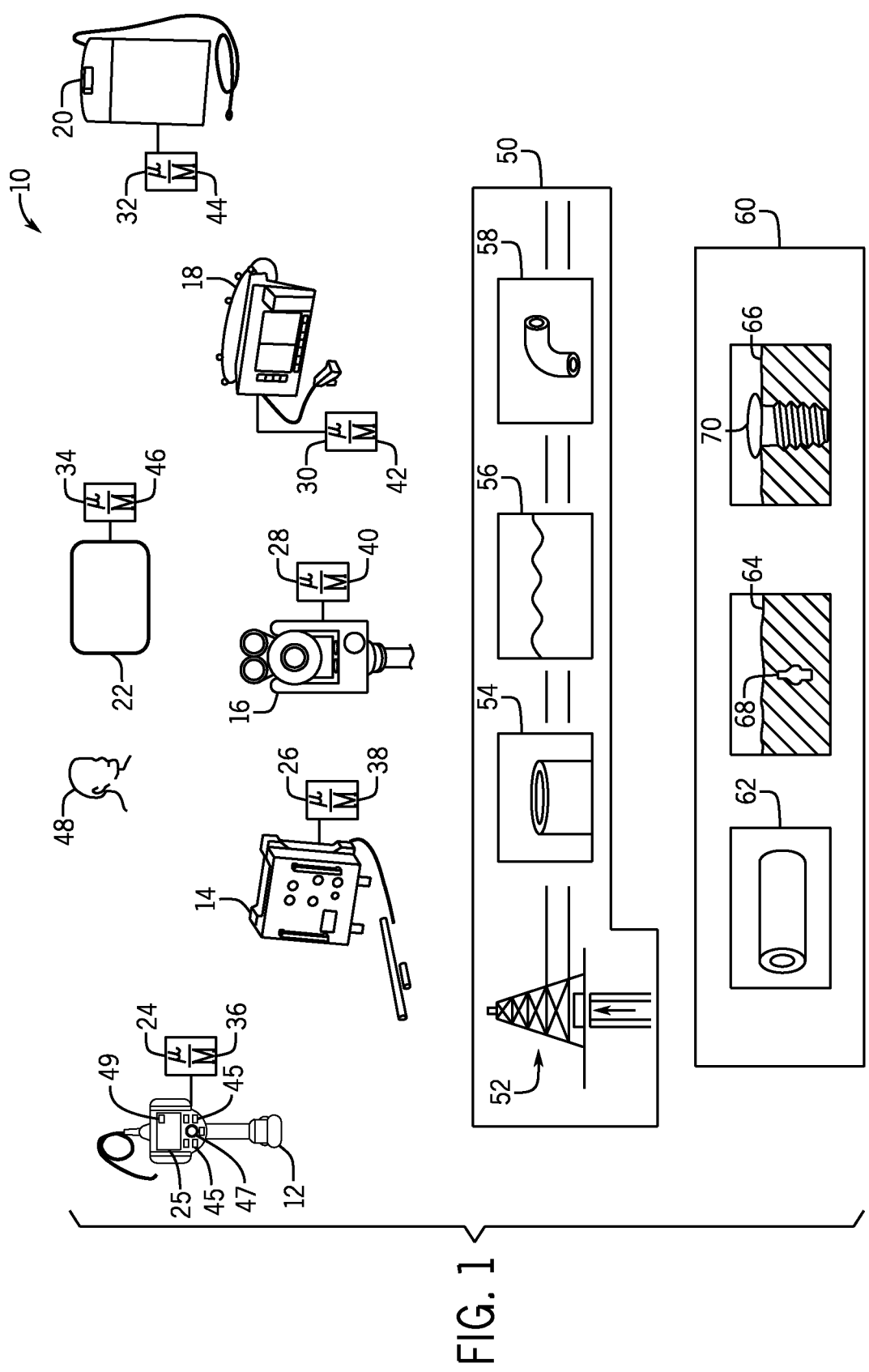
FIG. 1 illustrates embodiments of various non-destructive testing (NDT) devices, in accordance with the present embodiments.

With the foregoing in mind, it may be useful to describe embodiments of various non-destructive testing (NDT) devices, such as example NDT devices 10 as illustrated in FIG. 1. The NDT devices 10 may include any of various portable devices (e.g., mobile electronic devices) that may be useful in monitoring, analyzing, and providing visual inspection, for example, in a gas turbine system, a steam turbine system, a hydraulic turbine system, one or more compressor systems (e.g., aeroderivative compressors, reciprocating compressors, centrifugal compressors, axial compressors, screw compressors, and so forth), one or more electric motor systems, industrial systems including, for example, fans, extruders, blowers, centrifugal pumps, or any of various additional industrial devices or machinery that may be included in an industrial plant or other industrial facility.

In certain embodiments, as depicted in FIG. 1, the NDT devices 10 may include a video boroscope 12, an eddy current inspection device 14, a transportable pan-tilt-zoom (PTZ) camera 16, an ultrasonic flaw detector 18, a portable digital radiography device 20, an interface device 22, and so forth. The interface device 22 may include a mobile device (e.g., cell phone, laptop, tablet computer) that may be communicatively coupled to the aforementioned NDT devices 12, 14, 16, 18, 20 suitable for providing enhanced visualization (e.g., at a larger screen display), and for remote control and operations of the NDT devices 12, 14, 16, 18, 20. The NDT devices 12, 14, 16, 18, 20, 22 may be connected to each other and/or to local servers (e.g., local area network [LAN] servers), remote servers (e.g., wide area network [WAN] servers), and "cloud" based devices and services, near-field communication (NFC), and so forth. In one embodiment, the interface device 22 may be a MENTOR™ hardware device or software "app" executable via a mobile device (e.g., cell phone, tablet) available from General Electric Company, of Schenectady, N.Y. Likewise, the 12, 14, 16, 18, 20 devices may also be available from General Electric Company, of Schenectady, N.Y.

The depicted NDT devices 12, 14, 16, 18, 20, and 22 include respective processors 24, 26, 28, 30, 32, 34 and memory 36, 38, 40, 42, 44, and 46. The NDT devices 12, 14, 16, 18, 20, and 22 may additionally include a communications system suitable for communicating with other NDT devices 12, 14, 16, 18, 20, and 22 and with external systems such as "cloud" based systems, servers, computing devices (e.g., tablets, workstations, laptops, notebooks), and the like. The memory devices 36, 38, 40, 42, 44, and 46 may include non-transitory, tangible storage suitable for storing computer code or instructions useful in implementing various techniques described herein and may be executed via the respective processors 24, 26, 28, 30, 32, and 34. As will be further appreciated, the devices 12, 14, 16, 18, 20, and 22 may also include respective displays that may be used to display a graphical user interface (GUI) including multiple views of an image as well as inputs (e.g., touch buttons) to facilitate use of the devices 12, 14, 16, 18, 20, and 22. For example, the boroscope 12, which may be, for example, a video boroscope 12, may include a display 25 (e.g., liquid crystal display [LCD], organic light emitting display [OLED], etc.) that may be touch-sensitive (e.g., touch screen) and used to allow a user to interface and/or control the boroscope 12 and/or other NDT devices 14, 16, 18, 20, and 22. In addition, the boroscope 12 may include additional inputs such as physical buttons 45 and/or other input devices 47, such as a joystick, mouse ball, wheel, or other known input structure used to control the movement of an icon as part of the GUI.

Additionally, the GUI of the boroscope 12 may be able to present more than one image concurrently on the display 25. For example, a magnification window 49 may be displayed on the display 25 as part of the GUI of the boroscope 12 (or any other display displaying images of the various NDT devices 12, 14, 16, 18, 20, 22). In some embodiments, the magnification window 49 may represent a zoomed-in or magnified portion of the image displayed on display 25. For example, the magnification window 49 may display the portion of an image on the display at which an indicator of the GUI is overlaid on the image. In this manner, a user 48 may be able to view a portion of the image in greater detail by viewing the magnification window 49 and may be able to alter the location of the image presented in the magnification window 49 by moving the indicator of the GUI via, for example, an input device 47 and/or via touch input on the display 25. In other embodiments, as will be discussed in greater detail below, a user 48 may also be able to alter the location of the image presented in the magnification window 49 by interfacing with the magnification window 49 via, for example, an input device 47 and/or via touch input on the display 25.

In certain embodiments, as previously discussed, a user 48 (e.g., operator, field technician, engineer, and so forth) may utilize the NDT devices 12, 14, 16, 18, 20, 22 to inspect facilities 50, including facilities that may have equipment such as oil and gas equipment 52, and may include locations such as the interior of pipes or conduits 54, underwater (or underfluid) locations 56, and inaccessible or partially inaccessible locations such as locations having curves or bends 58, and so forth. Similarly, other systems 60 may also be inspected, such as aircraft systems, power generation systems (e.g., gas turbines, steam turbines, wind turbines, hydroturbines, combustion engines, generators, electric motors, and so forth), machinery (compressors, expanders, valves, actuators, and so forth), and the like, that may include conduits 62, various surfaces 64 and 66, and may be used to find undesired cracks 68 or to visualize parts 70, among many other uses.

Figure 2:
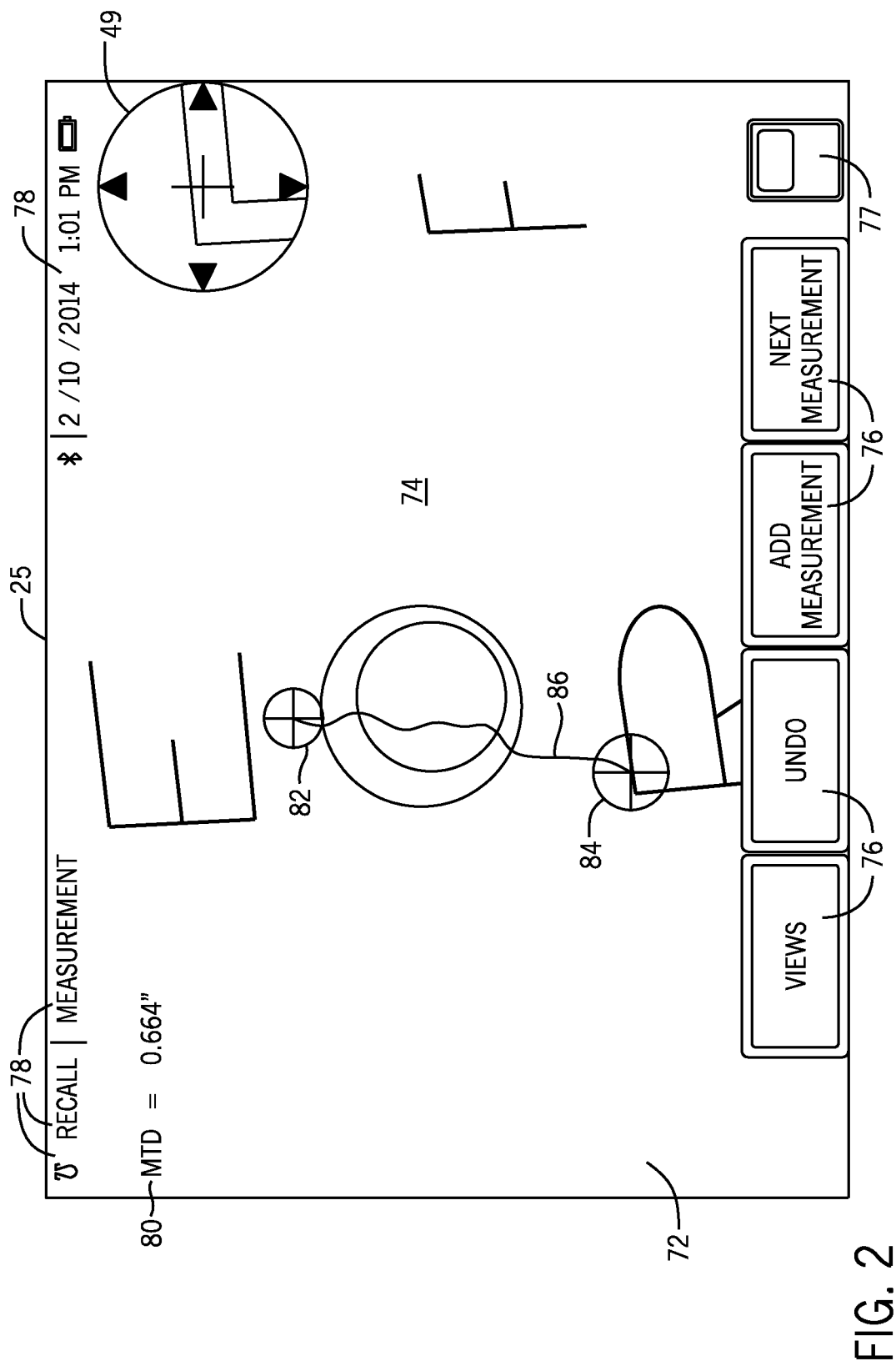
FIG. 2 illustrates a screenshot of the display of FIG. 1, in accordance with the present embodiments.

FIG. 2 illustrates a screenshot of a display 25 that may be generated to aid a user 48 in inspecting facilities 50 and/or systems 60. The display 25 may be a display internal to (e.g., housed within) a respective NDT device 12, 14, 16, 18, 20, 22 utilized to inspect the facilities 50 and/or systems 60. In other embodiments, the display 25 may correspond to a display of a workstation remote from (e.g., separate from) the respective NDT device 12, 14, 16, 18, 20, 22. In this embodiment, the remote workstation may communicate with the respective NDT device 12, 14, 16, 18, 20, 22 (e.g., via a communications system therein) to control the respective NDT device 12, 14, 16, 18, 20, 22 and the operation thereof. Thus, while FIG. 2 will be discussed from the perspective of a boroscope 12 with an internal display 25, it may be appreciated that the discussion below also corresponds to additional NDT devices 14, 16, 18, 20, 22 and/or remote workstation displays coupled to the respective NDT devices 12, 14, 16, 18, 20, 22.

As illustrated in FIG. 2, display 25 may display a GUI 72 over an image 74 being captured by the boroscope 12. This GUI 72 may allow a user to interact with and control the boroscope 12. In some embodiments, the GUI 72 may include various layers, windows, screens, templates, elements, or other components that may be displayed in all, or a portion, of the display 25. Generally, the GUI 72 may include graphical elements that represent applications and functions of the boroscope 12. The graphical elements may include representations of virtual buttons 76, virtual toggle button 77, menu bars and/or status information 78, measurement information 80, indicators 82 and 84, and the like. In certain embodiments, physical buttons 45 and/or other input devices 47 may be used to cause the processor 24 to display the GUI 72. For example, in response to actuation of the physical buttons 45 and/or other input devices 47, the horoscope 12 may display the menu bars and/or status information 78, measurement information 80, indicators 82 and 84, and the like. Additionally, a user 48 may interface with the virtual buttons 76, virtual toggle button 77, menu bars and/or status information 78, measurement information 80, and indicators 82 and 84 via a touch screen included in the display 25.

For example, when a virtual button 76 is selected, the horoscope 12 may open an application associated with that virtual button 76 and display a corresponding screen. Indeed, for each virtual button 76, a corresponding application that may include various GUI elements may be opened and displayed on the display 25. In some embodiments, as will also be further appreciated, selecting any of the virtual buttons 76 may also cause the display 25 of the horoscope 12 to display additional virtual buttons useful in providing additional options to the user 48. In some embodiments, the user 48 may further perform one or more touch gestures (e.g., pinch and zoom, double tap, etc.) or other selection techniques via interaction with the display 25 of the horoscope 12 to change or adjust the information presented on the display 25. This may be in place of or in addition to providing inputs via physical buttons 45 and/or other input devices 47.

Additionally, in some embodiments, virtual toggle button 77 may be utilized to toggle between a first set and a second set of operations assigned to virtual buttons 76. In this manner, additional operational flexibility may be provided to the user 48 without overly cluttering the display 25, as additional processes (selectable by the virtual buttons 76) may be accessible to the user 48 via the virtual toggle button 77.

In some embodiments, the GUI 72 may be represented in addition to an image 74 being captured by the horoscope 12. This image 74 may correspond to live video monitoring, freeze-frame image monitoring, image recall, and so forth of the horoscope 12. The GUI 72 may provide, for example, indicators 82 and 84 that may allow the user 48 (e.g., operator, technician, engineer, and so forth) to mark items of interest in the image for review. For example, a crack 86 may be present on an inspection item and the user 48 may place indicator 82 at a first portion (start) of the crack 86 and may place indicator 84 at a second portion (end) of the crack 86. The interaction of the user 48 with the horoscope 12 in this manner (e.g., via the GUI 72) may allow for inspection of the crack 86 to aid in diagnosing problems with an item being inspected with the horoscope 12.

In one embodiment, selection of one of the indicators 82, 84 (for example, indicator 84) by touch or via other input devices 47 may cause the processor 24 to generate a magnification window 49. This magnification window 49 may provide a magnified view of the portion of the image that corresponds to the selected indicator 84. In some embodiments, this magnification may be a magnification level of 2×, 3×, 4×, 5×, 10×, 20×, or more with respect to the representation of image 74. In some embodiments, the selected indicator 84 may flash, may be shaded temporarily, may change colors, or may otherwise visually indicate to a user 48 that the respective indicator 84 has been selected by the user 48. Once selected, user 48 interaction with the indicator 84 may cause movement of the selected indicator 84 with respect to the image 74. This may be useful to, for example, alter the distance between indicators 82 and 84 so that a user may be able to determine the length of the crack 86 therebetween.

Likewise, movement of the selected indicator across image 74 will cause the magnification window 49 to alter the region of image 74 being magnified. In this manner, magnification window 49 will display a magnified portion of image 74 which corresponds to the location of the selected indicator 84. Likewise, if a user 48 selects a different indicator 82, then the magnification window 49 will display a magnified portion of image 74 which corresponds to the location of the selected different indicator 82.

In some embodiments, movements of the indicators 82 and 84 via touch or via other input devices 47 may not allow for fine adjustments in moving the location of the indicators 82 and 84. Likewise, when using touch to move indicators 82 and 84, the finger of a user 48 may obscure the region of interest in the image 74 to be viewed. Accordingly, a user 48 may be unable to quickly, conveniently, and easily fine tune movement of the indicators 82 and 84 so as to, for example, allow for a detailed examination of a particular portion of image 74 via the magnification window 49. Accordingly, in some embodiments, fine (fractional) movements of the selected indicator (e.g., indicator 84) may be accomplished via user 48 interaction with the magnification window 49.

Figure 3:
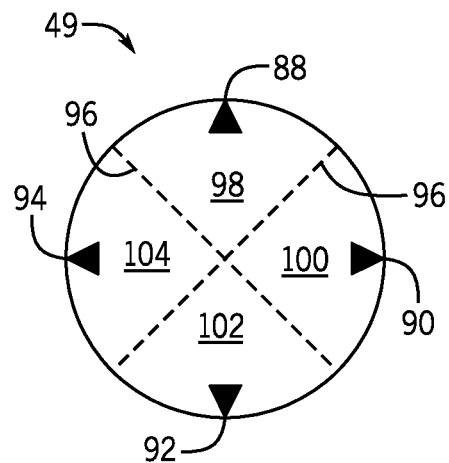
FIG. 3 illustrates an embodiment of the magnification window of FIG. 2, in accordance with the present embodiments.

FIG. 3 illustrates the magnification window 49 in greater detail. The magnification window 49 may include directional indicators 88, 90, 92, and 94. Additionally, in some embodiments, magnification window 49 may be divided by demarcation lines 96 into regions 98, 100, 102, and 104. These demarcation lines 96 may optionally be visible to the user 48 as part of the GUI 72. As illustrated, directional indicator 88 may be associated with region 98, directional indicator 90 may be associated with region 100, directional indicator 92 may be associated with region 102, and directional indicator 94 may be associated with region 104. However, it should be noted that the regions 98, 100, 102, and 104 may be further subdivided by additional demarcation lines such that additional regions correspond to each of directional indicators 88, 90, 92, and 94.

In some embodiments, a user 48 may select a directional indicator 88, 90, 92, or 94 so as to fractionally move the region inclusive of the magnified image in the direction corresponding to the directional indicator 88, 90, 92, or 94 selected. In some embodiments, this fractional movement of the image corresponds to movement equal to a width of five pixels of the display 25, two pixels of the display 25, one pixel of the display 25, ½ a pixel of the display 25, ⅓ a pixel of the display 25, ¼ a pixel of the display 25, ⅕ a pixel of the display 25, ⅒ a pixel of the display 25, 1/20 a pixel of the display 25, or another fractional amount of the movement across image 74 generated via a similar input made to indicator 82 or 84. In some embodiments, selection of directional indicator 88 will cause the portion of image 74 rendered in magnification window 49 to move towards the topmost portion of image 74. Likewise, selection of directional indicator 90 will cause the portion of image 74 rendered in magnification window 49 to move towards the rightmost portion of image 74. Similarly, selection of directional indicator 92 will cause the portion of image 74 rendered in magnification window 49 to move towards the bottommost portion of image 74. Finally, selection of directional indicator 94 will cause the portion of image 74 rendered in magnification window 49 to move towards the leftmost portion of image 74.

In this manner, a user 48 may alter the portion of the image 74 displayed with magnification in magnification window 49. In some embodiments, a user 48 need not interface with directional indicators 88, 90, 92, and 94 to cause the above-noted movement to occur. Instead, interaction with any of the regions 98, 100, 102, or 104 or the borders around regions 98, 100, 102, or 104 will have the same result (e.g., movement of the portion of the image 74 magnified) as selection of the directional indicator 88, 90, 92, or 94 that corresponds to the selected region 98, 100, 102, or 104. This selection technique may be in addition to or in place of interaction with the directional indicators 88, 90, 92, and 94.

In some embodiments, interaction with the directional indicators 88, 90, 92, and 94 and/or regions 98, 100, 102, and 104 by the user 48 will cause the directional indicators 88, 90, 92, and 94 and/or regions 98, 100, 102, and 104 to flash, to be shaded temporarily, to change colors, or may otherwise visually indicate to a user 48 that the respective indicators 88, 90, 92, and 94 and/or regions 98, 100, 102, and 104 has been selected by the user 48 and/or that movement has occurred. Additionally, the time that a user 48 interacts with the magnification window 49 may impact the amount of movement across the image 74 therein. For example, by pressing and holding the directional indicators 88, 90, 92, and 94 and/or regions 98, 100, 102, and 104 by the user 48 may cause continuous respective fractional movement of the portion of the image 74 being magnified. Likewise, a single touch by the user may correspond to a single fractional movement (e.g., the width of a pixel of the display 25 or a fractional width of a pixel of the display 25) of the portion of the image 74 being magnified.

In some embodiments, inputs received via the magnification window 49 may also cause the selected indicator 82 or 84 to move by an associated amount. In this manner, movement of the indicators 82 and 84 impacts the image presented in magnification window 49 and inputs received in magnification window 49 also impacts the location of the selected indicator 82 or 84. In some embodiments, the magnification window 49 may be shaped similar to or different from the indicators 82 and 84. However, while circular indicators 82 and 84 and magnification window 49 are illustrated, it is understood that the indicators 82 and 84 as well as magnification window 49 may also be sided shapes (e.g., square, triangular, rectangular, etc.).

Figure 4:
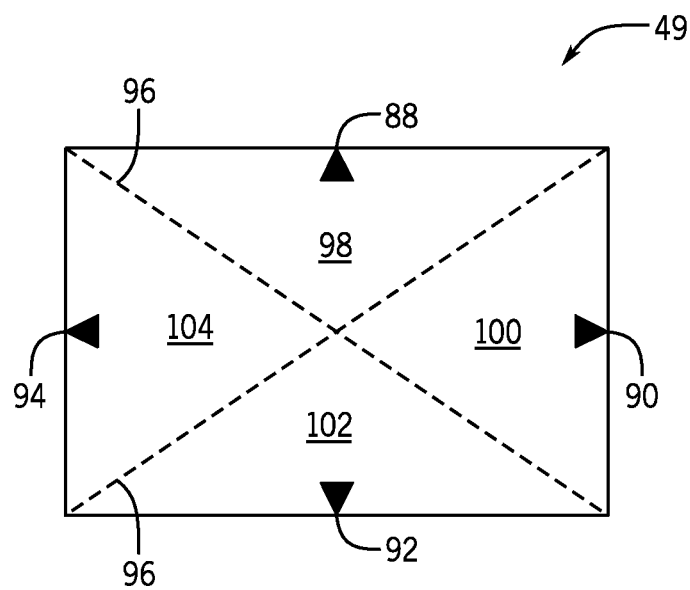
FIG. 4 illustrates a second embodiment of the magnification window of FIG. 2, in accordance with the present embodiments.

FIG. 4 illustrates an embodiment in which magnification window 49 is sized to be a sided shape (e.g. a rectangle). It may be understood that the discussion of FIG. 3 above with respect to the magnification window 49 also applies to the magnification window 49 of FIG. 4. Additionally, it should be noted that the magnification window 49 may provide additional views instead of/in addition to magnification of image 74. For example, contrast enhancements, differing dynamic ranges of the image 74, alternate views of the image 74, and/or other enhancements of the image 74 may be presented in place of, or in addition to, the magnification in window 49. Regardless of the image enhancement presented to a user 48, the technique of fractional movement via interaction with the window 49, as discussed above, would be available. Likewise, it may be appreciated that the techniques outlined above may be implemented via the processor 24 in conjunction with instructions stored in the memory 36 as part of the operation of the boroscope 12. Technical effects of the present application include providing an image and an enhanced portion of that image to a user. Additionally, interaction with an interface may allow for the user to adjust the portion of the enhanced image to be altered. Likewise, the ability to fractionally alter which portion of the image is being enhanced is provided. In some embodiments, fractional movement of the enhanced image may occur via interaction with the enhanced image itself or graphical elements associated therewith. In this manner, precise movements of a cursor or other indicator in a portion of a primary image via inputs received in the magnification window (e.g. in a portion of the display separate from the image of the indicator on a primary image) may be accomplished. In this way, the user (e.g., operator, technician, engineer, and so forth) may be able to view a primary image and modify a portion that is enhanced without impacting the ability to view the primary image. This may allow for greater ease of interaction with the NDT device's graphical user interface (GUI), thus facilitating and improving the use and user-friendliness of such devices in various testing and inspection applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable non-destructive testing (NDT) device, comprising:
   a processor configured to:
      receive imaging data of an item being inspected by the NDT device, wherein the imaging data is captured via a sensor of the NDT device;
      cause a display of the NDT device to display an image to be analyzed based on the imaging data, wherein the image comprises a fault present in the item being inspected by the NDT device;
      cause the display to display a graphical user interface (GUI), wherein the GUI is configured to render:
         a first indicator in a user selectable first portion of the display corresponding to a portion of the image having the fault; and
         a window configured to display a portion of the image corresponding to a location of the first indicator, wherein the GUI is configured to receive an indication of a first user interaction with the first portion of the display corresponding to the portion of the image having the fault, and wherein the GUI is configured to render the first indicator on or adjacent to the portion of the image having the fault in response to the first user interaction; and cause the first indicator to move to a second portion of the display corresponding to a second portion of the image having the fault in response to receiving an indication of a second user interaction with the window.

2. The device of claim 1, wherein the processor is configured to cause the first indicator to move to the second portion of the display in response to the user touching a predetermined portion of the window.

3. The device of claim 2, wherein the processor is configured to cause the first indicator to move to the second portion of the display in response to a duration of time that the user touches the predetermined portion of the window.

4. The device of claim 1, wherein the processor is configured to display a magnified portion of the image as the portion of the image corresponding to the location of the first indicator.

5. The device of claim 1, wherein the processor is configured to cause the display to display a second indicator concurrently with the first indicator, wherein the GUI is configured to render the second indicator in a user selectable third portion of the display corresponding to a third portion of the image having the fault, and wherein the GUI is configured to render the second indicator on or adjacent to the third portion of the image having the fault in response to a third user interaction with the display corresponding to the third portion of the image having the fault.

6. The device of claim 5, wherein the processor is configured to display in the window a second portion of the image corresponding to a location of the second indicator in response to determining that the second indicator has been selected by the user.

7. The device of claim 6, wherein the processor is configured to cause the second indicator to move to a fourth portion of the display in response to a fourth user interaction with the window subsequent to the determination that the second indicator has been selected by the user.

8. A non-transitory computer-readable medium having computer executable code stored thereon, the code comprising instructions to:

receive captured imaging data of an item being inspected by a portable non-destructive testing (NDT) device;

generate image data for display of an image on a display based on the captured imaging data, wherein the image comprises a fault present in the item being inspected by the NDT device;

generate a graphical user interface (GUI) for display on the display in conjunction with the image data, wherein the GUI is configured to render:

a first indicator in a user selectable first portion of the display corresponding to a portion of the image having the fault; and a window configured to display a portion of the image corresponding to the location of the first indicator, wherein the GUI is configured to receive an indication of a first user interaction with the first portion of the display corresponding to the portion of the image having the fault, and wherein the GUI is configured to render the first indicator on or adjacent to the portion of the image having the fault in response to the first user interaction; and modify the GUI to cause the first indicator to move to a second portion of the display corresponding to a second portion of the image having the fault in response to receiving an indication of a second user interaction with the window.

9. The non-transitory computer-readable medium of claim 8, wherein the code comprises instructions to cause the first indicator to move to the second portion of the display in response to receiving an indication of where the second user interaction with the window occurred.

10. The non-transitory computer-readable medium of claim 8, wherein the code comprises instructions to cause the first indicator to move to the second portion of the display in response to receiving an indication of how long the second user interaction with the window occurred.

11. The non-transitory computer-readable medium of claim 8, wherein the code comprises instructions to modify the GUI to cause the display to display a second indicator located in a user selectable third portion of the display.

12. The non-transitory computer-readable medium of claim 11, wherein the code comprises instructions to modify the GUI to cause the display to display a second portion of the image corresponding to a location of the second indicator in the window in response to determining that the second indicator has been selected by the user.

13. The non-transitory computer-readable medium of claim 12, wherein the code comprises instructions to modify the GUI to cause the second indicator to move to a fourth portion of the display in response to a user interaction with the window subsequent to the second indicator having been selected by the user.

14. A system, comprising:

an image capture device configured to capture an image of at least a portion of an industrial device or machinery being inspected by a portable non-destructive testing (NDT) device, wherein the image comprises a fault present in the industrial device or machinery;

a display configured to display the image; and a processor communicatively coupled to the an image capture device and the display and configured to cause the display to display a graphical user interface (GUI) on the display, wherein the GUI is configured to render:

a first indicator in a user selectable first portion of the display corresponding to a portion of the image having the fault; and a window configured to display a portion of the image corresponding to a location of the first indicator, wherein the GUI is configured to receive an indication of a first user interaction with the first portion of the display corresponding to the portion of the image having the fault, wherein the GUI is configured to render the first indicator on or adjacent to the portion of the image having the fault in response to the first user interaction, and wherein the processor is configured to cause the first indicator to move to a second portion of the display corresponding to a second portion of the image having the fault in response to receiving an indication of a second user interaction with the window.

15. The system of claim 14, wherein the image capture device, the display, and the processor are part of a common device.

16. The system of claim 14, wherein the image capture device is part of a first device and the display and the processor are part of a second device.

17. The system of claim 14, wherein the processor is configured to display an enhanced portion of the image as the portion of the image corresponding to the location of the first indicator.

18. The system of claim 14, wherein processor is configured to update the window to display a second portion of the image corresponding to the location of the first indicator at the second portion of the display in the window.

19. The device of claim 1, wherein the GUI comprises a user selectable interface corresponding to an indicator generation application, wherein user selection of the user selectable interface initiates the indicator generation application, such that a subsequent user interaction with the first portion of the display generates the first indicator.

20. The device of claim 5, wherein the GUI comprises a user selectable interface corresponding to a measurement application, wherein user selection of the user selectable interface initiates the measurement application, such that a subsequent user interaction with the first and the second indicators displays measurements corresponding to the first and the second indicators, such that the measurements indicate physical properties of the fault present in the item.

* * * * *